US008820010B2

(12) United States Patent
Abruña et al.

(10) Patent No.: US 8,820,010 B2
(45) Date of Patent: Sep. 2, 2014

(54) JALOUSIE WINDOW WITH DAYLIGHTING AND SHADING SHELF

(76) Inventors: Fernando L. Abruña, San Juan, PR (US); Jesús M. Sosa, San Juan, PR (US)

(*) Notice: Subject to any disclaimer, the term of this patent is extended or adjusted under 35 U.S.C. 154(b) by 0 days.

(21) Appl. No.: 13/280,011

(22) Filed: Oct. 24, 2011

(65) Prior Publication Data

US 2012/0102856 A1    May 3, 2012

Related U.S. Application Data

(60) Provisional application No. 61/407,347, filed on Oct. 27, 2010.

(51) Int. Cl.
| | |
|---|---|
| E06B 3/68 | (2006.01) |
| A61B 17/04 | (2006.01) |
| A61F 2/24 | (2006.01) |
| A61B 17/00 | (2006.01) |

(52) U.S. Cl.
CPC ..... *A61F 17/0401* (2013.01); *A61B 2017/0409* (2013.01); *A61B 2017/0417* (2013.01); *A61B 2017/0477* (2013.01); *A61B 2017/0496* (2013.01); *A61B 2017/0488* (2013.01); *A61F 2/2442* (2013.01); *A61B 2017/00469* (2013.01); *A61B 2017/0464* (2013.01); *A61B 2017/0475* (2013.01); *A61B 17/0487* (2013.01); *A61B 2017/00243* (2013.01); *A61B 2017/0419* (2013.01); *A61B 2017/0406* (2013.01); *A61B 2017/0046* (2013.01)
USPC ....... 52/204.6; 52/204.51; 359/591; 359/597; 49/80.1

(58) Field of Classification Search
USPC ......... 52/204.51, 204.6, 204.66, 73; 359/591, 359/597; 49/73.1, 80.1
See application file for complete search history.

(56) References Cited

U.S. PATENT DOCUMENTS

| | | | | |
|---|---|---|---|---|
| 270,832 | A * | 1/1883 | Nolan | 49/51 |
| 3,060,529 | A * | 10/1962 | Clay | 49/58 |
| 4,027,430 | A * | 6/1977 | Sakamoto | 49/403 |
| 4,509,825 | A * | 4/1985 | Otto et al. | 359/592 |
| 4,688,351 | A * | 8/1987 | Torres | 49/74.1 |
| 4,899,491 | A * | 2/1990 | Okumoto | 49/62 |
| 5,778,598 | A * | 7/1998 | Ohanesian | 49/74.1 |
| 5,802,784 | A * | 9/1998 | Federmann | 52/204.5 |
| 6,098,339 | A * | 8/2000 | Rivera et al. | 49/74.1 |
| 6,239,910 | B1 * | 5/2001 | Digert | 359/596 |
| 6,378,248 | B1 * | 4/2002 | Jordal | 49/80.1 |
| 6,480,336 | B2 * | 11/2002 | Digert et al. | 359/596 |
| 6,988,525 | B2 * | 1/2006 | Moulton | 160/52 |
| 7,222,456 | B1 * | 5/2007 | Carey | 49/73.1 |
| 7,940,460 | B2 * | 5/2011 | Braunstein et al. | 359/591 |
| 8,027,092 | B1 * | 9/2011 | Huff et al. | 359/591 |
| 8,116,004 | B2 * | 2/2012 | Griffiths | 359/591 |
| 2001/0019451 | A1 * | 9/2001 | Digert et al. | 359/596 |
| 2003/0112518 | A1 * | 6/2003 | Rogers et al. | 359/596 |
| 2004/0256062 | A1 * | 12/2004 | Moulton | 160/89 |
| 2007/0277458 | A1 * | 12/2007 | Graboyes | 52/232 |

(Continued)

*Primary Examiner* — Brian Glessner
*Assistant Examiner* — Joshua Ihezie
(74) *Attorney, Agent, or Firm* — Duane Morris LLP

(57) ABSTRACT

A window assembly defines a transom opening above a movably deployable reflective shelf that is positionable to reflect sunlight into the building through the transom, and also can be closed over the transom for protection and/or privacy. The reflective shelf may be associated with a mechanically operated a jalousie window. A plurality of shading shelves may be located on the window below the reflecting shelf and similarly operable to open and close.

8 Claims, 6 Drawing Sheets

(56) References Cited

U.S. PATENT DOCUMENTS

| | | | |
|---|---|---|---|
| 2009/0272037 A1* | 11/2009 | Sosa | 49/74.1 |
| 2010/0149643 A1* | 6/2010 | Hooper, Jr. | 359/596 |
| 2010/0208454 A1* | 8/2010 | Braunstein et al. | 362/127 |
| 2010/0254011 A1* | 10/2010 | Griffiths | 359/597 |
| 2010/0258113 A1* | 10/2010 | Hyatt | 126/704 |
| 2011/0315330 A1* | 12/2011 | Huff et al. | 160/368.1 |
| 2012/0180957 A1* | 7/2012 | Svirsky | 160/59 |

\* cited by examiner

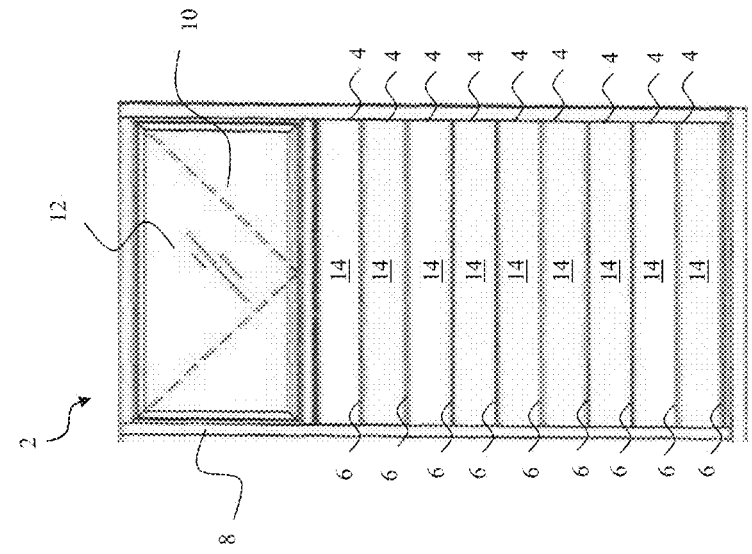
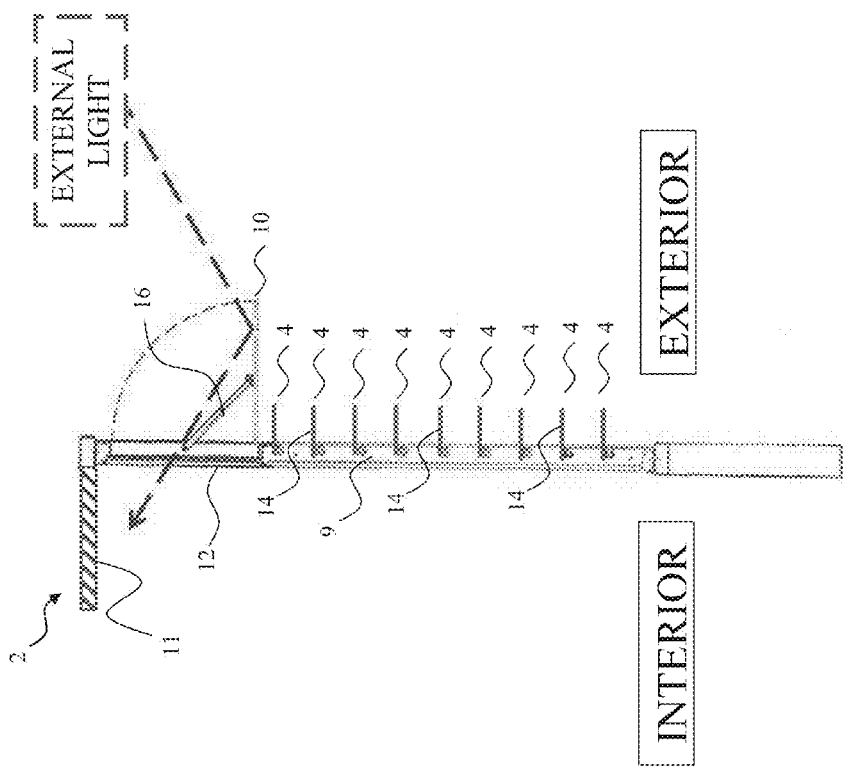
FIG. 2
FIG. 1

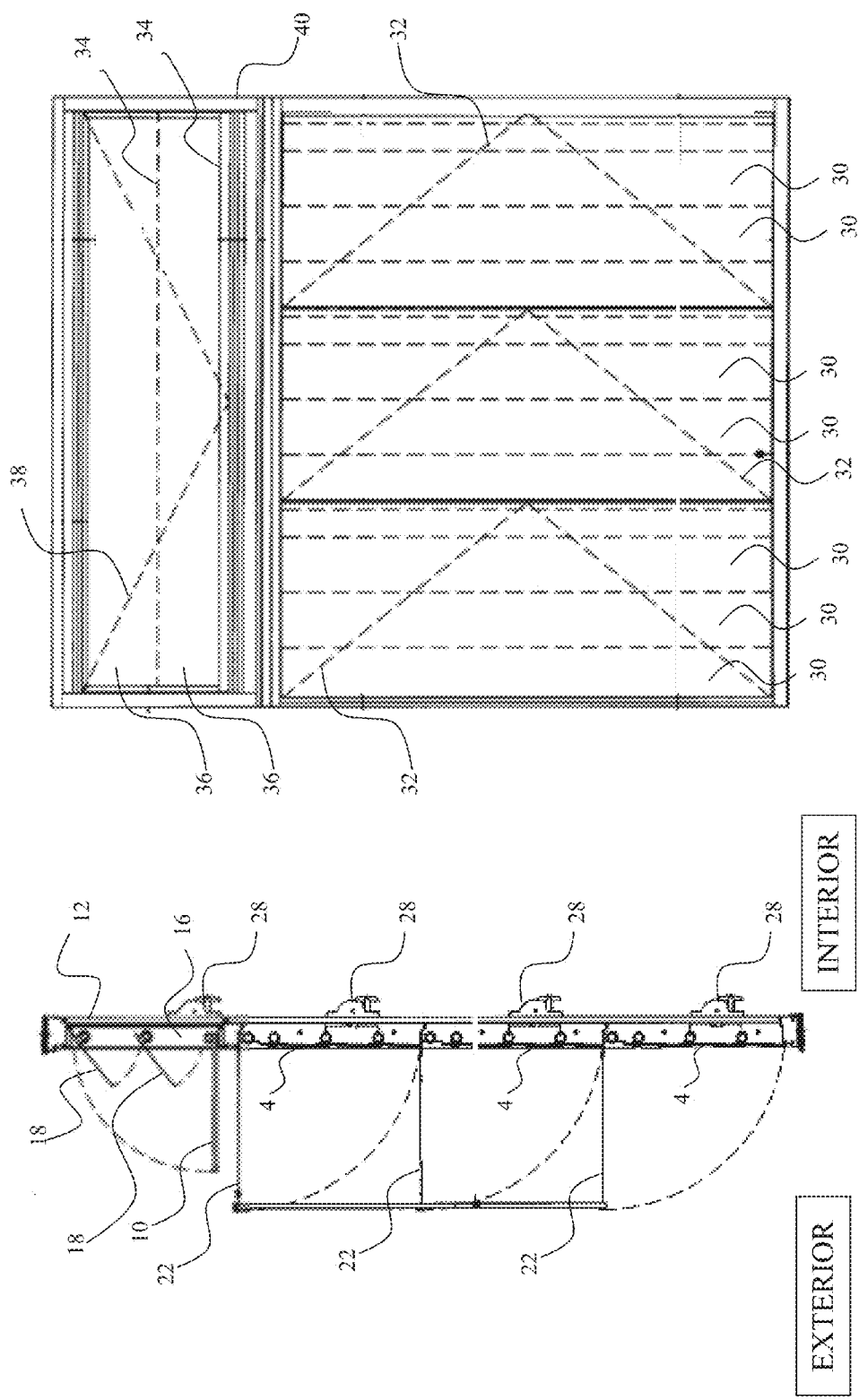

JALOUSIE WINDOW WITH DAYLIGHTING AND SHADING SHELF

CROSS REFERENCE TO RELATED APPLICATION

This application claims priority of U.S. Provisional Patent Application No. 61/407,347, filed Oct. 27, 2010, which is hereby incorporated by reference.

FIELD OF THE INVENTION

The disclosure relates to window structures, and in particular concerns a building exterior window assembly having a movable reflective shelf positioned below a transom, wherein the reflective shelf is configured to direct exterior light through the transom and into the building, and movable opaque shading shelves positioned in between groups of transparent slats to maintain them in shade.

BACKGROUND

A building window typically comprises a rectangular frame, often constructed from extruded lengths of metal or polymer or another material. The frame is arranged in an opening in a building wall having a given depth or wall thickness, and the frame carries a glass unit. In some windows, the glass is stationary and seals the opening. Advantageously, however, the glass unit can comprise a fixed pane and an overlapping movable sash pane, or two slidably overlapping sashes, one or more hinged casements, pocket panels or another movable structure by which the window is opened or shut selectively, namely by adjusting the position of its movable parts relative to the frame.

Windows have several useful aspects. These include, at least, admitting or blocking light and viewing, admitting or blocking air circulation, thermal insulation (conductive, convective and/or radiant) when closed, capacity to block rain or other precipitation or dampness, security against unauthorized entry or exit, etc. A window may be more or less effective for these particular functions due to the specific structure chosen. There are tradeoffs.

Windows also have important aesthetic effects. The size and character of an exterior window can vary the perceptions of those in a room in a building and those who view the window from the exterior. From the interior, for example, different sizes and structural arrangements can carry different impressions with respect to privacy and security versus public exposure, warmth in a cold climate or comfortable coolness in a hot climate. From the exterior, windows vary from welcoming expansive openings to forbidding security arrangements.

Among possible window structures, the jalousie type window comprises a plurality of slats or louvers that are mounted on parallel spaced pivot axes. Typically the pivot axes of the slats are horizontal but they can be vertical instead. The slats advantageously can be ganged by a linkage mechanism causing the slats to pivot open or closed in unison. Jalousies can have security benefits because the spacing between the slats is typically too small to admit an intruder in any pivot position of the slats. The slats can be pivoted into a position at least partly perpendicular to the plane of the building wall. When fully perpendicular, planar slats occupy the minimum cross sectional area obstructing air flow or view. Wholly planar parallel slat structures might be sized and spaced so as to pivot into a common plane when closed. Often the slats are configured for upper slats to overlap at their edges with lower slats when closed. In order to seal closed against the passage of air or light, the edges of the slats can have seals and/or can be shaped with stepped edges that are complementary to the shape of an adjacent slat. Slats may comprise sheet material that is flat, or curved across a lateral cross section. A curve tends to contribute stiffness. Slats may vary in thickness across a lateral cross section in a diamond or lozenge or other shape. These variations from a thin flat planar slat shape increase the apparent slat thickness when the slats are fully open.

Among other possible variations, the slats of a jalousie window can be relatively wider or narrower in a lateral direction perpendicular to the slat pivot axis, and might be centered and balanced on the pivot axis or off-center so as to cantilever when open. A smaller number of wider slats can encompass the same size window opening as a greater number of narrower slats, regardless of the relative placement of the pivot axis. But when the slats are opened, different arrangements produce different effects, for example as to sun shading, slat position and span of displacement of the slat edges in a direction perpendicular to the plane of the window, etc.

The jalousie slats can comprise clear glass, colored or translucent glass, or an opaque material such as sheet metal, wood or plastic, or painted or covered glass. Clear glass is desirable for viewing when opened or closed. Opacity is desirable for privacy when closed. A sheet metal material provides security.

Glass or otherwise transparent slats may promote interior illumination by allowing direct sunlight to enter the building through the glass. The direct light, however, may undesirably impact the interior temperature. The solar radiation may also damage the contents of the building or the jalousie slats themselves. Furniture and other upholstery may prematurely fade and wear. Glass jalousies may also present a security risk. They may allow malicious individuals on the exterior of the building to view interior contents, even when the slats are in a closed position. Additionally, glass slats may be easily broken by accident, malicious behavior, or environmental hazards.

In an effort to mitigate the concerns associated with glass jalousie slats, opaque alternatives may be used. Metal, wood, or plastic slats may shield a building's interior from harmful solar rays. They may also be more resilient and provide greater security from break-ins or environmental hazards. Opaque slats, however, may hinder the natural light entering a building. As a result, interior lighting solutions may be necessary. Additionally, while the opaque slats may protect the building's contents from damage, they are themselves susceptible to solar and environmental wear.

It would be desirable to provide a jalousie window assembly which promotes natural interior illumination, while avoiding the harmful side effects of solar rays. Doing so may be helpful in maintaining a comfortable and stable interior temperature in the building, and may impact energy costs by reducing the need for artificial lighting. Additionally, it would be desirable to provide an assembly which promotes this interior illumination without compromising the safety and security of a building's contents.

It would therefore be desirable to provide an apparatus which combines the illumination capabilities of transparent jalousies with the protective capabilities of opaque jalousies.

SUMMARY OF THE INVENTION

To address these and other needs, and in view of its purposes, the invention provides, according to one aspect, a window assembly comprising a window frame that includes a transom situated over at least one reflecting shelf, wherein the reflecting shelf is structured and oriented to direct exterior light through the transom and into the building.

The reflecting shelf may comprise any material that is at least somewhat reflective. When in an operable position, exterior light from a source at an elevation higher than the shelf (especially the sun), hits the shelf and is reflected inwardly or upwardly through the transom and into the building. The shelf may be positioned to direct the light towards an interior ceiling, which may itself be a reflective or light colored surface. In this manner, the interior of the building is naturally illuminated without exposing its contents or occupants to direct solar radiation.

The reflective shelf may be movable into a closed position. While in a closed position the shelf may completely or partially cover the transom. This may shield the transom from forced entry, precipitation, projectile objects, or the like. Such a shield may be particularly effective in areas prone to hurricanes or other natural storms. Alternatively, the shelf may be movable to protect an apparatus below the transom, such as a jalousie structure.

The window assembly may carry a jalousie configuration comprising a plurality of slats that are pivotal to open or closed positions. This jalousie structure may be mounted below the reflective shelf and is thereby shielded from direct exterior light at a high angle of incidence. Such a configuration prevents premature wear of the jalousie slats by limiting their exposure to solar radiation. In some embodiments, a jalousie configuration may also fill a space defined by the transom. This jalousie structure may be integral with, or independent of, the jalousie structure below the transom.

The transom may enclose around an empty space, a transparent or translucent material, an insect screen, a jalousie structure, etc. If a jalousie is provided at the transom, it may be independent of, integral with, or mechanically coupled or electrically driven to operate in conjunction with a jalousie structure positioned below the transom and reflecting panel. If the transom contains a jalousie structure, the jalousie slats may be made of a transparent or translucent material, such as glass, so as to allow the reflecting shelf to direct light through the transom, regardless of whether the slats are in an open or closed position.

The window assembly may have one or more shading shelves below the transom. These shelves may be movable between an open and a closed position. While in an open position, the shelves may shade the lower portion of the window from light not reflected by the reflecting shelf. This serves to further protect the interior of the building or the jalousie structure from direct sunlight. When in a closed position, the shading shelves may protect the window assembly in substantially the same manner as the reflective shelf may shield the transom. By reducing exposure to direct sunlight, the shading shelves may also limit solar heat gains on the interior of the building.

The shading shelves, jalousie assemblies, and reflecting shelf may all be independently operable. For example, the shading shelves and a lower jalousie structure may be closed while the reflecting tray and transom are open. This allows the structure to be changed to a variety of different configurations depending on a user's preference.

A number of additional aspects and embodiments will be made apparent in the following description of a range of nonlimiting examples and considerations according to which the preferred arrangements can be varied within the scope of the invention claimed.

BRIEF DESCRIPTION OF THE DRAWINGS

The invention is best understood from the following detailed description when read in conjunction with the accompanying drawing. It is emphasized that, according to common practice, the various features of the drawing are not necessarily to scale. On the contrary, the dimensions of the various features are arbitrarily expanded or reduced for clarity. Like numerals denote like features throughout the specification and drawing.

FIG. 1 is a cross-sectional view of a window apparatus in which external light is directed through a transom by a reflecting shelf;

FIG. 2 is a front elevation view of a window apparatus in which the reflecting shelf is in a closed position over the transom;

FIG. 7 is a cross-sectional view of a window apparatus in which the jalousies, reflecting shelf, and shading shelves are all on different control mechanism.

FIG. 8 is a front elevation view of a window apparatus, with the jalousies and shading shelves in a vertical orientation.

DETAILED DESCRIPTION

Figure 4:
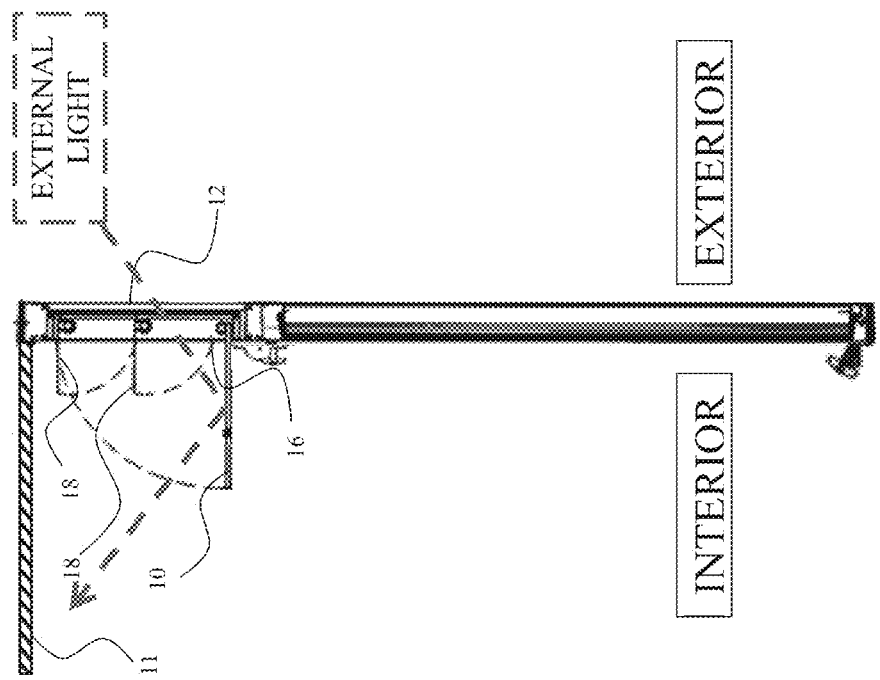
FIG. 4 is a cross-sectional view of a window apparatus depicting an open reflecting shelf and a transom comprised of a jalousie structure.

FIGS. 1 and 2 show one embodiment of a window apparatus 2 for promoting interior illumination while limiting exposure to solar radiation and ingress of heat energy. The window apparatus can be mounted in a number of specific ways, and in a given embodiment may include all or only parts of the aspects discussed herein as advantageous. By way of nonlimiting example, this discussion assumes that the view of FIGS. 1 and 2 are representative as the apparatus might be embodied, for example, as an exterior window bounding a room in a residential living space.

In one embodiment, window apparatus 2 defines a transom 12 oriented over a reflective shelf 10 and a jalousie structure 9. In this context, "transom" may be defined as referring to a framed opening associated with another opening such as a door or window, typically located as a clerestory above the upper part of the window or door opening, and permitting passage of light and/or air. Transom 12 may define an empty space when the shelf is open, or can comprise a sheet of glass, transparent or translucent plastic, insect screening, or any other permanent or removable light conductive material. Reflective shelf 10 is movably carried on a horizontal axis and is secured to frame 8 by hinged arm 16, thereby making it operable between an open and a closed position. As shown in FIG. 2, while in the closed position reflective shelf 10 covers or shields transom 12. When in the open position, as depicted in FIG. 1, the reflective shelf 10 is disposed below and outside of transom 12 and serves to reflect exterior light towards the interior of the building, while at the same time shading the lower jalousie structure 9. The jalousie structure 9 comprises parallel slats 4 also carried on horizontal axis so as to pivot at journals at opposite sides of window frame 8.

FIG. 1. shows reflective shelf 10 in an open position, meaning reflective shelf 10 is oriented into a plane at some angle relative to the plane of transom 12. In FIG. 1, reflective shelf 10 is oriented to 90 degrees, but the deployed angle may be adjustable preferably within a range of angles from acute to obtuse. While in its open position, reflective shelf 10 may direct light from an external source (e.g. sun, moon, stars, or street lamps) towards the interior of a building. In the shown embodiment, the light is redirected towards an interior ceiling 11 for deeper building penetration. The ceiling 11 may have a reflective surface, such as a coat of white paint, to further promote illumination. When in the closed position, the shelf 10 forms an outer panel disposed over the transom opening and as such can be an outer panel that functions in conjunction with an inner closure panel of glass or other material, or can be the sole structure by which the transom opening is caused to be opened or closed.

FIG. 2 shows reflective shelf 10 from a front elevation perspective, in an closed position, meaning that reflective shelf 10 is oriented into a plane substantially parallel to transom 12. While in a closed position, reflective shelf 10 may serve to cover or shield transom 12 from external elements. For example, reflective shelf 10 may protect the transom 12 from forced entry, rain, wind, hail, or airborne projectiles. The reflective shelf 10 may also shield the interior of the building from sunlight and solar radiation, thereby preserving interior temperatures and protecting furniture, upholstery, and the like from premature fading or wear. While in a closed position, the edges of reflective shelf 10 may abut window frame 8 so that no portion of transom 10 is exposed.

Reflective shelf 10 may be comprised of any material capable of reflecting any wave of the electromagnetic spectrum. In one embodiment the shelf comprises an aluminum sheet at the surface, painted white, but sheet metal, foil, plastic, wood, or reflective glass may also be used. An upper surface of the reflective shelf may be comprised of a reflective material or, in the case of glass, a mirror coating can be placed on the top or on the underside.

In FIGS. 1 and 2, the reflective shelf is attached to window frame 8 by hinged arm 16. This arm facilitates pivotal opening and closing of the shelf. It should be appreciated that other attachment mechanisms may be used to open and close reflective shelf 10. Alternatively or additionally, the shelf may be permanently or detachably mounted in an open position. The shelf may also be raised or slid, rather than lowered, into an open and operable position. In some embodiments, reflective shelf 10 may or may not shield transom 12 when in a closed position. The shelf may protrude outwards from the building, protrude into the building, or may have portions on both sides of the transom.

FIG. 2 shows the jalousie slats 4 in their closed position from the outdoor side, meaning that the respective front surfaces 14 of slats 4 are pivoted substantially into plane parallel to the plane of the frame 8 and the wall in which the window is mounted. In this embodiment, the closed slats form a substantially planar surface in combination, but it is also possible that when fully closed the slats could remain slightly inclined relative to the plane of the frame, for example in a case where the slats are substantially flat and an upper slat overlaps a lower one when closed.

The rotation axes of the depicted slats 4 are generally horizontal, i.e., parallel to the ground (not shown), i.e., the longitudinal axes of slats 4 extend left to right in the illustrated embodiment of FIG. 1. Adjacent slats 4 preferably abut each other such that opposed longitudinal edges 6 either abut each other or preferably overlap slightly such that a superjacent slat 4 overlaps a subjacent slat 4.

Each slat 4 is advantageously pivotally coupled to window frame 8 via a drive mechanism disposed in one or both opposite members of the frame. The slats may be attached via non-round fittings to a rotatable element in the frame having an eccentric crank arm. The crank arms of all the slats can be coupled in a parallelogram linkage to a mechanism such as a geared rotatable handle. Operating the handle lifts or lowers an element coupled with respect to one of crank arms in the linkage. Thus, operating the handle causes the linkage to rotate all the slats clockwise or counterclockwise on their axes to close or open the jalousie.

As shown in FIG. 1, the linkage can rotate the slats open from the rotational position such that the opposite lateral edges of each slat are moved closer to a horizontal plane parallel to the planes of each of the other slats. The slats preferably are rotatable up to 90° where the jalousie is fully open, or farther. When the slats are oriented edgewise, the slats provide a minimal obstruction to view by a person viewing inwardly or outwardly through window. When window apparatus 2 is fully open, front surfaces 14 of slats 4 may be substantially horizontal, i.e. front surfaces 14 occupy parallel planes substantially parallel to the ground thereby opening vertical spaces between adjacent slats 4 for air flow, line of sight to the horizon, etc.

Each slat 4 is preferably thin and flat. The slats can be arranged to admit light when closed, e.g., comprising clear or translucent spaced glass panes, spaced from one another and sealed together around their edges. The slats can be structured to be thermally insulative, e.g by including an insulation layer or case.

Figure 3:
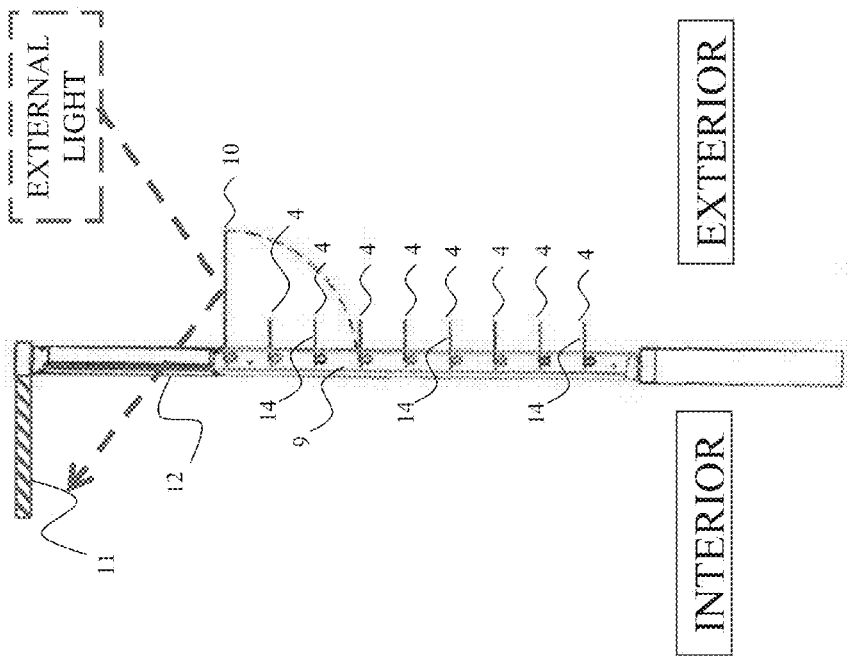
FIG. 3 is a cross-sectional view of a window apparatus depicting an open reflecting shelf integrated with an upper jalousie slat.

FIG. 3 shows an embodiment from a cross sectional perspective in which one of the jalousie slats 4 is integrated with reflective shelf 10. The integrated reflective shelf may be placed sufficiently near the top of the jalousie structure to facilitate light reflection through transom 12. In one embodiment, the reflective shelf 10 entirely supplants one of the jalousie slats 4. Alternatively, the integration may be facilitated through an adhesive, mechanical, or magnetic attachment.

FIG. 4 shows an embodiment in which the transom comprises a jalousie structure and reflective shelf 10 opens towards the interior of a building. The transom jalousie structure 16 may be comprised of a plurality of horizontal slats 18, wherein the structure and slats are substantially similar to the jalousie structure described above. Reflective shelf 10 may be oriented below the transom and configured to reflect external lighting into the building.

The transom jalousie slats 18 may be made of glass, clear or translucent plastic, or any other material suitable for windows. Such a material may allow reflective shelf 10 to reflect light, even when the slats 18 are in a closed position. The material also permits light to reach the ceiling 11 of the structure when the slats 18 are in an open position. In one embodiment, slats 18 have a reflective lower surface to facilitate further control of the light redirected from reflective shelf 10. In such an embodiment, the exterior light may first be reflected off the reflective shelf, and reflected a second time off the slats.

Transom jalousie structure 16 and jalousie structure 9 may be the same structure. In such an embodiment, a plurality of slats may be pivotally coupled to window frame 8 and oriented substantially parallel to the ground. The window may be bisected by reflecting shelf 10 at a location below the top of the window frame, thereby creating a transom. This allows the reflecting shelf to direct exterior light through an opening between the slats or, if the slats are made of a transparent or translucent material, through the slats themselves. It may also allow all the slats to be operated from a single control mechanism. This configuration may be particularly beneficial for already installed jalousie windows in which a transom may not already be defined.

Figure 6:
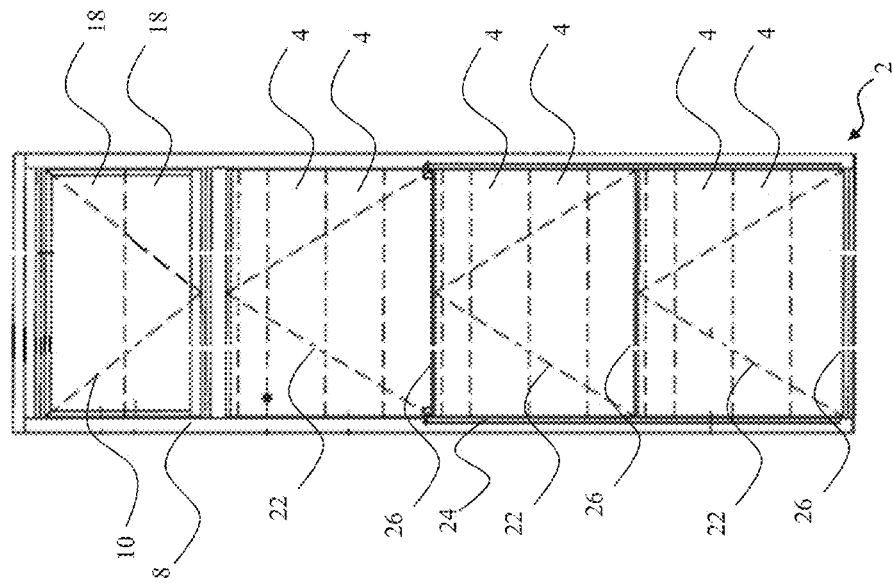
FIG. 6 is a front elevation view of a window apparatus in which the shading shelves and reflecting shelf are in a closed position.
Figure 5:
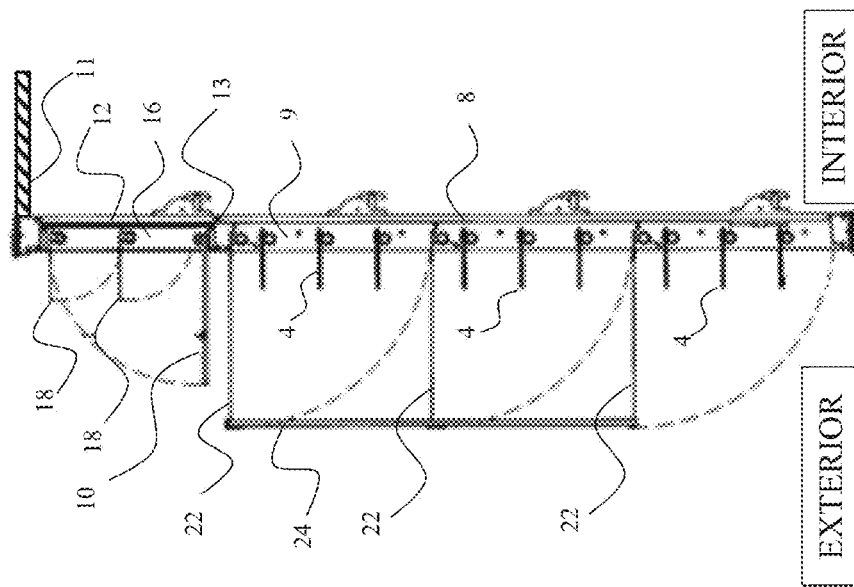
FIG. 5 is a cross-sectional view of a window apparatus showing shading shelves and a reflecting shelf in an open position.

Turning now to an alternative or additional feature of the present disclosure, FIGS. 5 and 6 show an embodiment of the window apparatus for promoting interior illumination while further reducing solar exposure. The window apparatus defines a transom 12 oriented above reflective shelf 10 and jalousie structure 9. Reflective shelf 10 is carried on a horizontal axis and is pivotally secured to frame 8 by journals 13, thereby making it operable between an open and a closed position.

The lower jalousie structure 9 comprises parallel slats 4 also carried on horizontal axis so as to pivot at journals at opposite sides of window frame 8. Transom 12 comprises an upper jalousie structure 16 and a plurality of transom slats 18 carried on horizontal axis so as to pivot at journals at opposite sides of transom 10. A plurality of shading shelves 22 are carried along a horizontal axis and are pivotally coupled to frame 8 below the reflecting shelf 10, thereby making them operable between an open and a closed position. Corner guard 24 is pivotally coupled to the exterior corners of the shading shelves.

FIG. 5 is shows shading shelves 22 in an open position from a cross sectional perspective, meaning the shading shelves are oriented into a plane at some angle relative to the plane of window frame 8. In FIG. 5 this angle is 90 degrees, but other angles are also acceptable. When in their open configuration, shading shelves 22 may shield the slats 4 and the building interior from direct sunlight, while at the same time permitting air flow and line of sight to the horizon. Combining the shading shelves 22 with reflecting shelf 10 permits this obstruction of sunlight without compromising a building's natural interior illumination. By obscuring direct sunlight, the shading shelves reduce the building's interior exposure to destructive solar radiation and also reduces solar heat gains.

In one embodiment, shading shelf 22 and reflecting shelf 10 are the same shelf. In such an embodiment the shelf may have an upper reflective layer substantially similar to the reflective shelf discussed above. The reflective layer may reflect exterior light into the building while also shading any lower shading shelves or jalousie slats.

FIG. 6 shows an embodiment of window apparatus 2 from a front elevation perspective. Slats 4 and 18, reflective shelf 10, and shading shelves 22 are all in a closed position, meaning that they are pivoted substantially into a plane parallel to the plane of the frame 8 and the wall in which the window is mounted. In this embodiment, the closed shading shelves 22 form a substantially planar surface in combination, but it is also possible that when fully closed the shading shelves 22 could remain slightly inclined relative to the plane of the frame, for example in a case where the shelves are substantially flat and an upper shelf overlaps a lower one when closed.

The rotation axes of the depicted shading shelves 22 are generally horizontal, i.e., parallel to the ground (not shown), i.e., the longitudinal axes of shading shelves 22 extend left to right in the illustrated embodiment of FIG. 6. Adjacent shading shelves 22 preferably abut each other such that opposed longitudinal edges 26 either abut each other or preferably overlap slightly such that a superjacent shading shelf 22 overlaps a subjacent shading shelf 22. In this manner the shading shelves 22 may substantially cover or shield the lower jalousie structure 9 and its corresponding slats 4, thereby protecting them from forced entry, solar radiation, rain, wind, hail, airborne projectiles, or the like. When both the shading shelves and the reflecting shelf are closed, a room may be rendered substantially dark.

Each shading shelf 22 may be pivotally coupled to window frame 8 via a drive mechanism. The drive mechanism can pivot the shading shelves 22 open from the pivot position such that the opposite lateral edges of each shelf are moved closer to a horizontal plane parallel to the planes of each of the other shading shelves 22. The shading shelves 22 preferably are rotatable up to 90° where they are fully open, or farther.

In one embodiment, the reflective shelf, the shading shelves, or both may be insulated. Additionally, the edges of the reflective shelf and one or more shading shelves may overlap to reduce or eliminate the escape of air conditioned or heated air from the interior of the building.

FIG. 7 depicts an embodiment in which the slats 4 and 18, reflective shelf 10, and shading shelves 22 are each controlled by independent control devices 28. Controlling each element independently allows for a variety customizable configurations. FIG. 7 depicts a configuration where the lower slats are closed, the transom slats are partially open, and the reflective shelf and shading shelves are both completely open. The control devices 28 may be concealed in window frame 8 to protect them against weather or vandalism.

FIG. 8 depicts an embodiment in which the shading shelves and jalousie slats are in a vertical orientation. Slats 30 are parallel and their longitudinal axes are oriented vertically with respect to the ground (not shown). Similarly, Shading shelves 32 are parallel and their longitudinal axes are oriented vertically with respect to the ground. Both slats 30 and shading shelves 32 may be pivotally coupled to window frame 40. Reflecting tray 38 covers transom 34 and is pivotally coupled to window frame 40. Transom jalousie slats 36 are in a horizontal orientation and are in a closed position.

Figure 9:
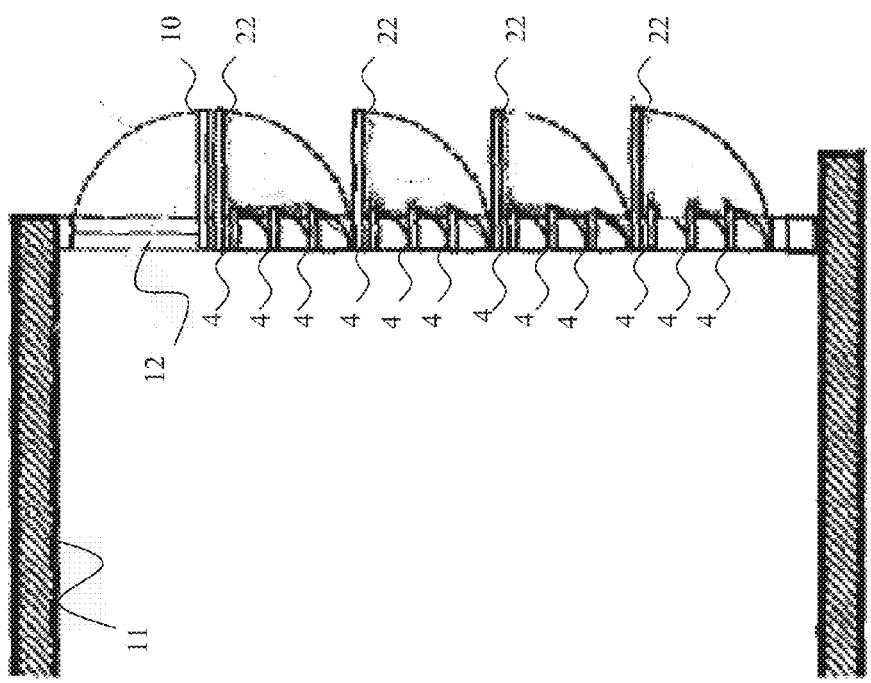
FIG. 9 is a cross-sectional view of a window apparatus configured for optimal natural ventilation.

FIGS. 9-12 demonstrate different configurations of the window apparatus that may be beneficial in specific scenarios. FIG. 9 depicts a plurality of jalousie slats 4 in an open position, four shading shelves 22 in a raised position, and reflective shelf 10 in a lowered position. This configuration is designed to enhance natural ventilation by permitting airflow past the jalousie slats 4.

Figure 10:
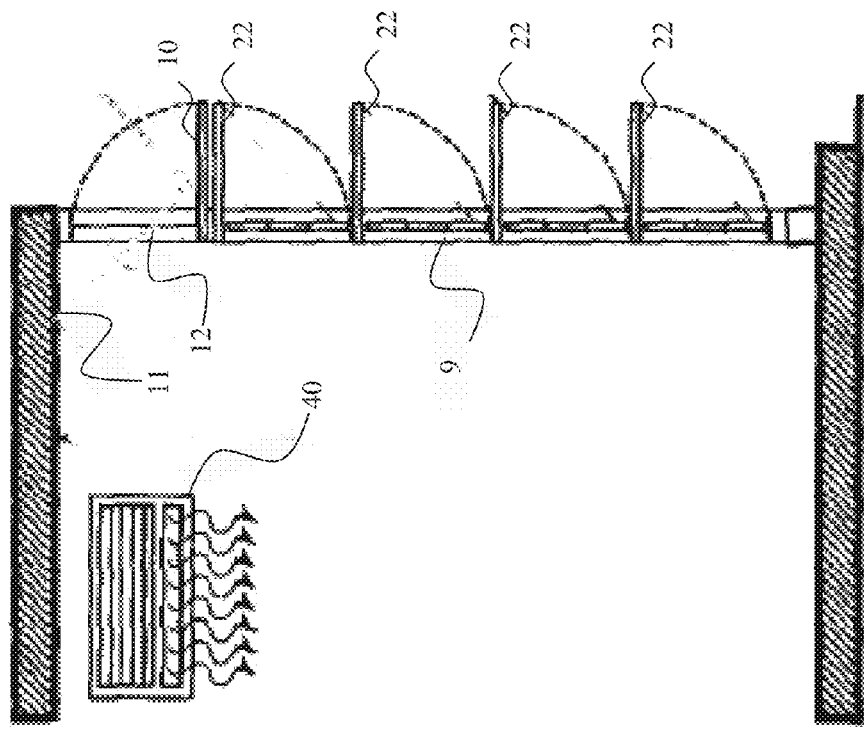
FIG. 10 is a cross-sectional view of a window apparatus configured for retaining air-conditioned air.

FIG. 10 depicts jalousie structure 9 in a closed position, shading shelves 22 in a raised position, and reflective shelf 10 in a lowered position. Air-conditioning unit 40 releases air-conditioned air into the room. Closing jalousie structure 9 may prevent the escape of the air-conditioned air, while still promoting natural interior illumination through transom 12. Alternatively or additionally, unit 40 may be configured to release heated air.

Figure 11:
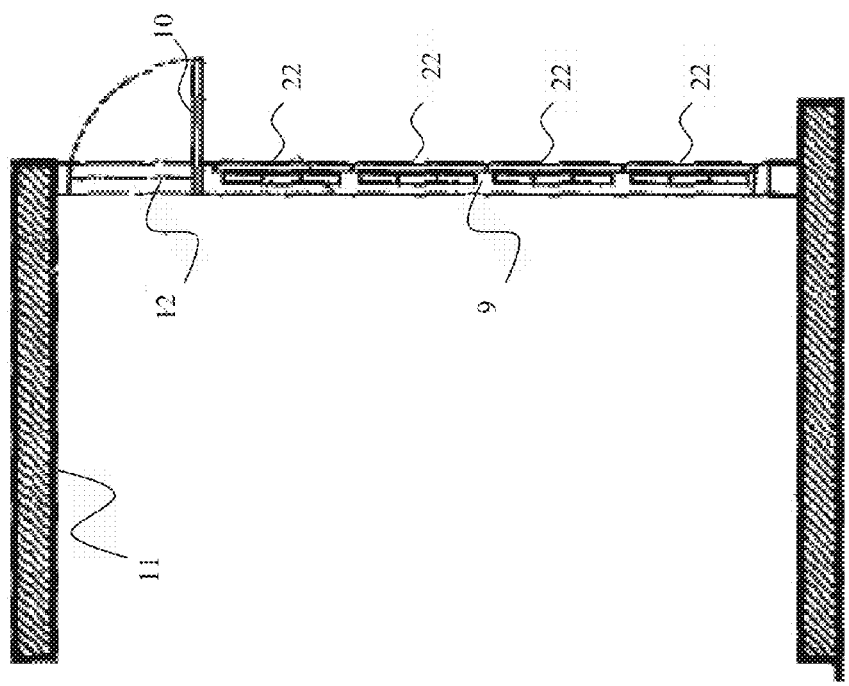
FIG. 11 is a cross-sectional view of a window apparatus configured for privacy.

FIG. 11 depicts a window apparatus configuration for enhancing privacy. Jalousie structure 9 and shading shelves 22 are both in a closed position. This may prevent view from the exterior of the structure to the interior. Reflective shelf 10 is in a lowered position to allow exterior light to penetrate transom 12 and illuminate the building.

Figure 12:
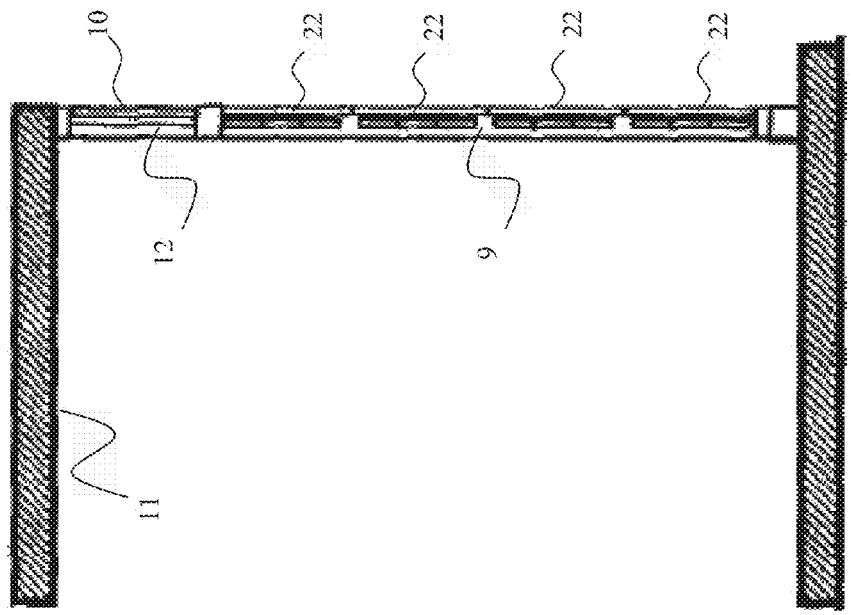
FIG. 12 is a cross-section view of a window apparatus configured for hurricane protection.

FIG. 12 depicts the window apparatus configured for hurricane protection. Shading shelves 22 are in a closed position so as to cover jalousie structure 9. Similarly, reflective shelf 10 is in a closed position to cover transom 12. By covering the jalousie structure 9 and the transom 12, the reflective shelf 10 and shading shelves 22 may protect the window structure from damage. In the case of a hurricane, they may deflect airborne projectiles such a tree limbs or sand.

The preceding examples illustrate the principles of the invention. It will thus be appreciated that those skilled in the art will be able to devise various arrangements which, although not explicitly described or shown herein, embody the principles of the invention and are included within its spirit and scope.

The examples and associated conditional language found in this disclosure are for instruction in understanding the principles of the invention and demonstrate general and specific methods, structures and concepts that differ from the art. However, the invention should be construed in accordance with the appended claims and not limited to the embodiments disclosed as examples. Statements reciting principles, aspects, and embodiments of the invention the specific examples thereof, encompass structural and functional equivalents, including currently known equivalents and equivalents that may yet be developed to similarly perform the same function, regardless of structure.

In discussing the embodiments shown in the drawings and other examples, this description uses various relative terms such as "lower," "upper," "horizontal," "vertical," "above," "below," "up," "down," "top" and "bottom" as well as derivatives thereof (e.g., "horizontally," "upwardly," etc.). These terms should be construed to refer to the orientation as then described or as shown in the drawing under discussion, and do not imply that the invention is necessary limited to a similar orientation or relative arrangement of parts. Similarly, terms concerning attachments, coupling and the like, such as "coupled", "connected" and "interconnected," refer to a relationship wherein structures are secured or attached to one another either directly or indirectly through intervening structures, as well as both movable or rigid attachments or relationships, unless otherwise apparent from the disclosure and context.

The appended dams defining the invention should be construed broadly to include other variants and embodiments of the invention, which may be made by those skilled in the art without departing from the scope and range of equivalents of the invention as disclosed.

What is claimed is:

1. A window assembly, comprising:
    a window frame configured for mounting in an opening in a wall of a building, defining a plane between an inside of the building and an outside of the building;
    a jalousie structure comprising a plurality of jalousie slats that are one of transparent and translucent and are mounted in the window frame on spaced axes, the jalousie slats being controllably movable toward the plane for closing a space defined by the window frame and pivotable out of the plane for opening spaces between the jalousie slats;
    a shelf structure comprising a plurality of shelves mounted to said window frame together with the jalousie slats on axes parallel to the spaced axes of the jalousie slats, wherein the shelves are opaque and each of the shelves is controllably movable toward the plane, to close over the space defined by the window frame outside at least two of the jalousie slats that are adjacent to the respective said shelf, wherein the shelves are pivotable out of the plane into a position perpendicular to the plane and extending from the plane toward the outside of the building, each of said plurality of shelves shading a group of at least two jalousie slats that are behind and below the respective said shelf;
    wherein an uppermost one of the shelves is reflective and covers over an uppermost plurality of the jalousie slats, the uppermost one of the shelves being mounted on an axis spaced below a top of the window frame and operable to pivot toward the plane to a position closing over the window frame and into an open position outward from the plane wherein the uppermost one of the shelves is arranged for reflecting outside light inwardly through the window frame.

2. The window assembly of claim 1, wherein the plurality of shelves comprise a material that is at least somewhat reflective on an outside, such that each of the shelves directs sunlight away from the adjacent at least two jalousie slats that are behind and below the shelf.

3. The window assembly of claim 1, wherein the plurality of shelves are adjacent to one another when closed and substantially cover over the space defined by the window frame below an uppermost one of the shelves.

4. The window assembly of claim 1, wherein the space between the top of the window frame and the axis of the uppermost one of the shelves comprises a light transmitting transom.

5. The window assembly of claim 1, wherein the shelves and the jalousie slats are operably coupled to a common control device.

6. The window assembly of claim 1, wherein the axes of the plurality of shelves are spaced from the axes of the at least two of the jalousie slats that are adjacent thereto and wherein the shelves are operably coupled to a first control device and the axes of the jalousie slats are operably coupled to a second control device.

7. The window assembly of claim 1, wherein plural adjacent jalousie slats in adjacent said groups of at least two jalousie slats that are coverable by said shelves are movable by a control common to the jalousie slats in the adjacent groups.

8. The window assembly of claim 7, wherein the shelves operable to cover said adjacent groups have a control independent of the control common to the jalousie slats in said adjacent groups.

* * * * *